United States Patent [19]

Strawder

[11] Patent Number: 5,640,439
[45] Date of Patent: Jun. 17, 1997

[54] APPARATUS FOR POSITIONING A PATIENT FOR TAKING AN X-RAY

[76] Inventor: Glenn G. Strawder, 3405 Robey Terr. Apt. 302, Silver Spring, Md. 20904

[21] Appl. No.: 567,038

[22] Filed: Dec. 4, 1995

Related U.S. Application Data

[63] Continuation-in-part of Ser. No. 265,111, Jun. 24, 1994, Pat. No. 5,473,664, which is a continuation-in-part of Ser. No. 820,075, Jan. 13, 1992, Pat. No. 5,226,068.

[51] Int. Cl.$^6$ ................................................. G03B 42/02
[52] U.S. Cl. ........................... 378/177; 378/167; 378/172
[58] Field of Search ....................................... 378/167, 169, 378/177, 178, 180, 204, 208, 209, 170, 172

[56] References Cited

U.S. PATENT DOCUMENTS

| | | |
|---|---|---|
| 2,478,597 | 8/1949 | Scarpellino . |
| 2,571,011 | 10/1951 | Chapman ................................. 378/178 |
| 3,293,430 | 12/1966 | Wustner . |
| 3,622,783 | 11/1971 | Miller . |
| 3,916,207 | 10/1975 | Reed . |
| 4,114,044 | 9/1978 | Chiulli . |
| 4,333,014 | 6/1982 | Renshaw . |
| 4,352,197 | 9/1982 | Waerve . |
| 4,399,552 | 8/1983 | Renshaw . |
| 4,414,683 | 11/1983 | Robinson . |
| 4,455,672 | 6/1984 | Hahn . |
| 4,700,373 | 10/1987 | Miller . |
| 5,022,065 | 6/1991 | Wijkstrom . |
| 5,133,000 | 7/1992 | Moller . |
| 5,226,038 | 7/1993 | Strawder . |
| 5,473,664 | 12/1995 | Strawder . |

Primary Examiner—Don Wong

[57] ABSTRACT

A device for positioning a patient adjacent an X-ray cassette has a plate on which a part of a human body may be located and a socket adjacent the plate. The socket has least one slot or cavity in it. This slot or cavity will receive X-ray cassettes of different thicknesses. Forces for holding the cassettes upright are provided to reduce the width of the slot by biasing two cams to engage against the lower portion of the cassettes.

7 Claims, 3 Drawing Sheets

APPARATUS FOR POSITIONING A PATIENT FOR TAKING AN X-RAY

RELATED CASES

This application is a continuation-in-part of my prior U.S. patent application Ser. No. 08/265,111 filed Jun. 24, 1994, entitled Method of and Apparatus for Positioning a Patient for the Taking of an X-ray, now U.S. Pat. No. 5,973,664, which application was in turn a continuation-in-part of my U.S. patent application Ser. No. 07/820,075 filed Jan. 13, 1992, now U.S. Pat. No. 5,226,068.

BACKGROUND OF THE INVENTION

This invention relates to a device for holding an X-ray film cassette while an X-ray of a part of the body of either a human being or of an animal is being taken.

In the practice of emergency medicine it is frequently necessary to make an X-ray of a part of a human body that has been seriously injured and cannot be moved in response to the requests of an X-ray technician who has been asked to take an X-ray. Frequently, the X-ray technician has difficulty in positioning the part of the body of the patient, that is to be X-rayed, relative to the X-ray cassette.

The prior art discloses means for positioning a patient adjacent a cassette that holds an X-ray film. For example Waerve, U.S. Pat. No. 4,352,197 has a mounting device for positioning a cassette carrying an X-ray film between the patient and a table.

Scarpellino, U.S. Pat. No. 2,478,597 shows a "head and shoulder" rest for use in supporting body parts while X-rays are passed through the body.

Moreover, positioning devices for X-ray cassettes are shown in the following U.S. Pat. Nos.: Wustner 3,293,430; Reed 3,916,207; Robinson 4,414,683; Miller 4,700,373; Moller 5,133,000; Chiulli 4,114,044; and Wijkstrom 5,022,065.

SUMMARY OF THE INVENTION

The invention includes a plate and a socket near one end of said plate. The socket has at least one slot or cavity in it. This slot or cavity will receive X-ray cassettes. Means are employed to hold X-ray cassettes of different thicknesses upright in said slot. In the preferred form of the invention, these means comprise one or more cams biased to engage the lower border of an X-ray cassette to clamp it against one side of the cavity and thus hold the cassette upright. A part of a human body to be X-rayed is placed on said plate and X-rays pass through said part and to said cassette. Since many X-ray cassettes have a film of smaller dimensions than the cross-section of the cassette, the fact that the cassette is in the slot insures that a portion of the part to be X-rayed is not cut-off on the X-ray film.

DETAILED DESCRIPTION OF THE INVENTION

Figure 1:
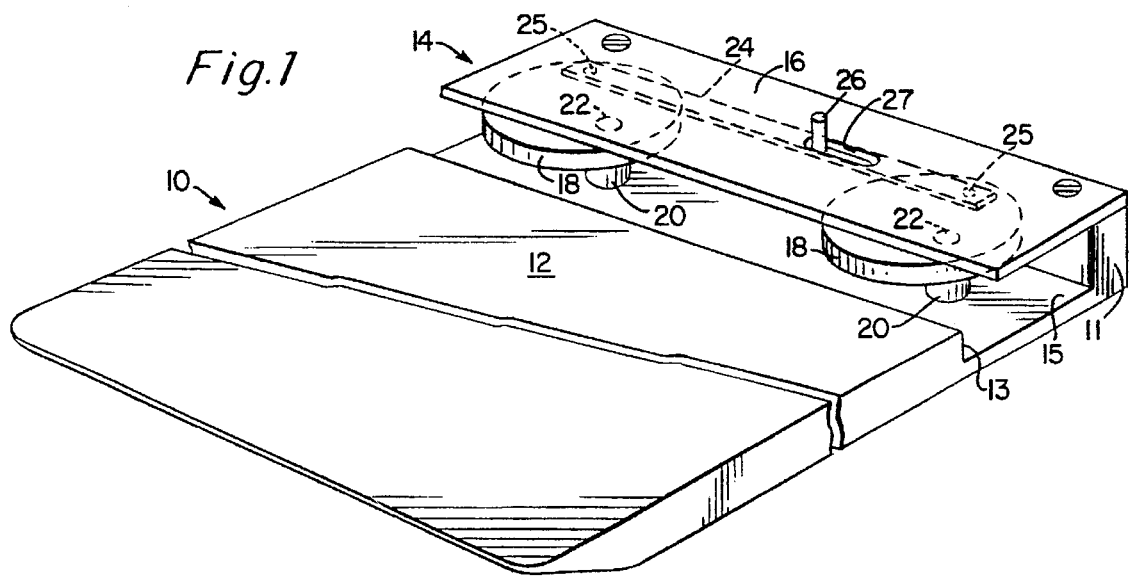
FIG. 1 is a perspective view of the preferred form of the invention.
Figure 2:
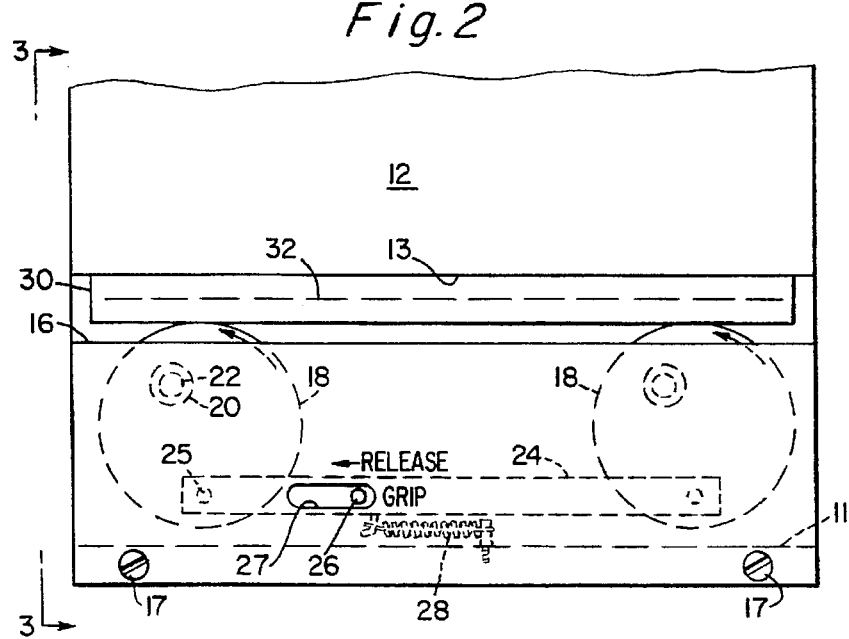
FIG. 2 is a top view of the device of FIG. 1, where the cams 18 are biased by spring 28 against an X-ray cassette 30.
Figure 3:
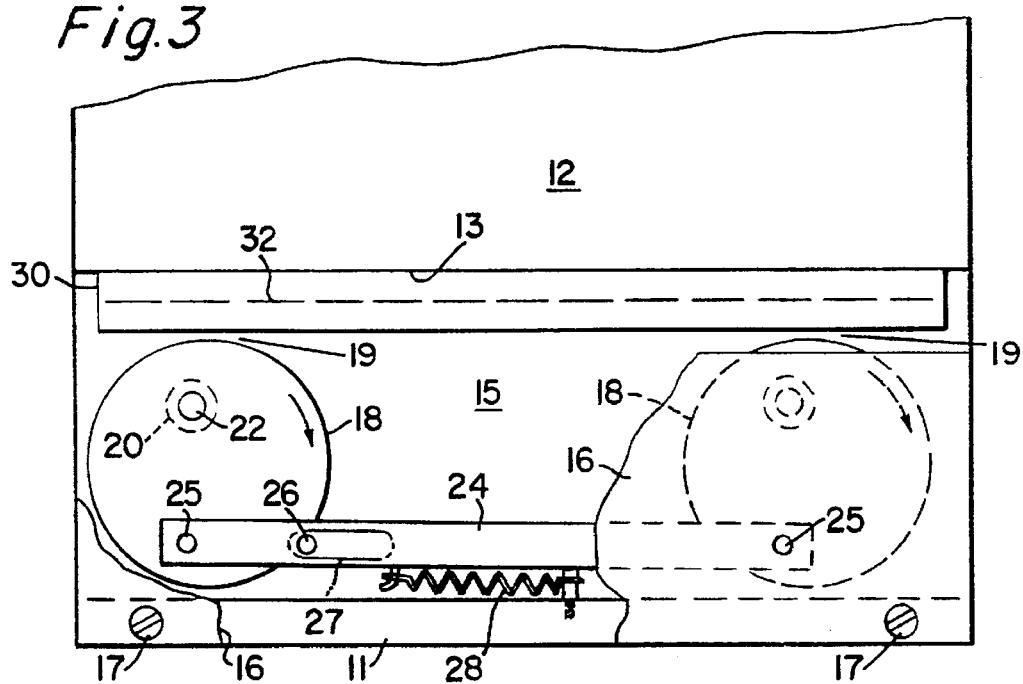
FIG. 3 is a top view of FIG. 1 where the cams 18 have been manually moved away from the cassette 30.
Figure 4:
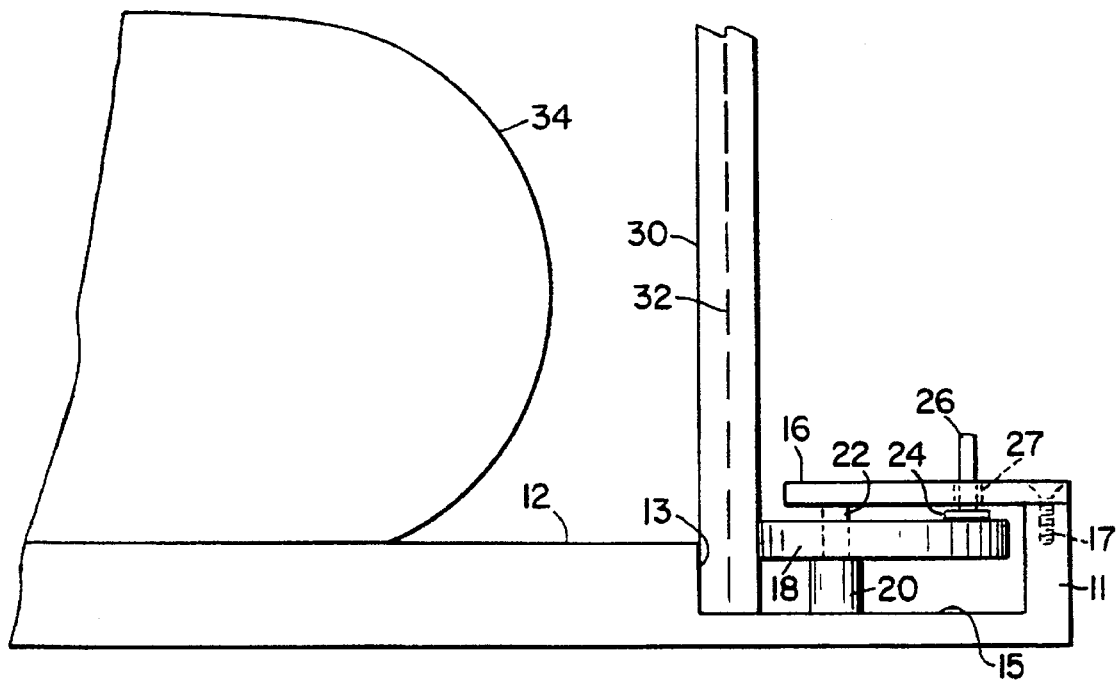
FIG. 4 is a side view of the device of FIG. 1.

As shown in FIG. 1, the plastic plate 10 has a top area 12 on which a part of a patient, for example, the patient's head, may be placed. The plate 10 has a vertical wall 13 which forms one side of a cavity 15 bounded on its other side by wall 11. Two cams 18 are mounted for rotation on pivots 22 which are supported on bosses 20. The bosses 20 may be part of the same piece of molded plastic as the plate 10. The cams 18 are interconnected by arm 24 which is pivoted to each cam 18 at pivots 25. A handle 26 is mounted on the arm 24. A cover plate 16 is supported by rear wall 11 and is affixed to wall 11 by screws 17.

In operation, the part of the patient to be X-rayed is placed on area 12. The X-ray technician then moves handle 26 in slot 27 to the right (FIG. 1) to open the space between the cams 8 and the wall 13. The X-ray cassette 30 (having a film 32) is then placed in the space between the cams 18 and the wall 13. The handle 26 is then released so that spring 28 will rotate the cams 18 counterclockwise. The cams 18 thus move against the lower border of cassette 30 and clamp that cassette between the cams 18 and wall 13. This clamping holds the cassette upright. The word upright as used herein means that the cassette is held in a plane suitable for the taking of an X-ray. X-ray's are then passed through the body part of the patient that is located on area 12 and thence to the cassette 30.

The wall 13 and the cams 18 define a cavity for receiving the cassette 30. This cavity is wider than the thickest cassette so that my device will work with any cassette, no matter how thick it is.

Figure 5:
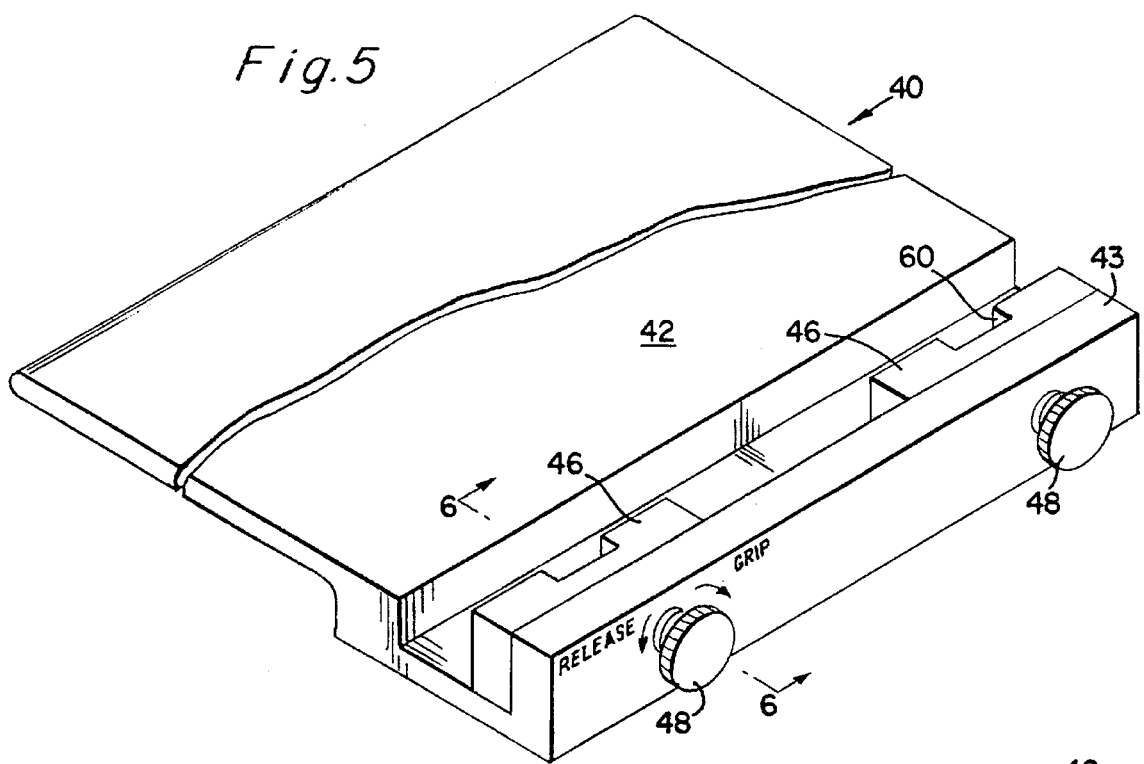
FIG. 5 is a perspective view of a modified form of the invention.
Figure 6:
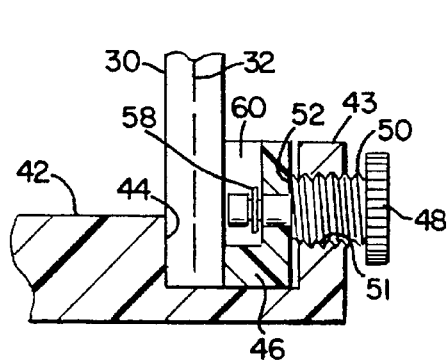
FIG. 6 is a detail view of the device of FIG. 5.
Figure 7:
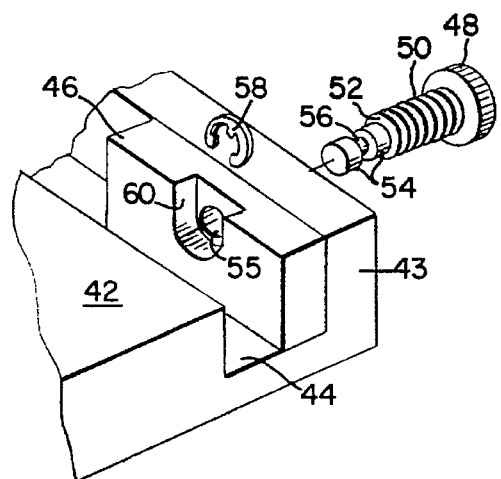
FIG. 7 is a perspective view of the details shown in FIG. 6.

The modified form of the invention shown in FIGS. 5, 6 and 7 has a plate 40 which receives the part of a patient to be X-rayed on face 42. A cavity formed between wall 44 and clamping member 46 is wider than the thickest X-ray cassette. The clamping member 46 is moved toward and away from wall 44 by the screw 50 which has knurled knob 48. The forward end 54 of screw 50 passes through hole 55 and cut-out 60. That forward end has an annular slot 56 for receiving C-spring 58. Thus, the screw 50 may rotate causing its threads to mate with threads 51 in wall 43. When screw 50 rotates, the clamping member 46 moves.

Assuming that the screw 50 has been fully rotated in the "release" direction (FIG. 5) there is a gap or cavity between wall 44 (FIG. 6) and clamping members 46. This gap or cavity is large enough to receive the thickest X-ray cassette. When an X-ray cassette of any thickness is inserted between wall 44 and clamping members 46, the knurled knobs 48 may be rotated to move clamping members 46 against the lower border of the X-ray cassette and hold the cassette upright (as previously defined).

I claim to have invented:

1. A device for positioning a part of a patient adjacent an X-ray cassette for the purpose of taking an X-ray, comprising:

a plate for receiving a part of a patient to be X-rayed, said plate defining at least one wall of an elongated cavity that forms a socket and has sufficient width to receive X-ray cassettes, said plate having an end, said cavity being adjacent said end, said plate having an area for receiving the part, of the patient, to be X-rayed, said cavity being located between said area and said end, and means for holding X-ray cassettes of different thicknesses upright in said socket, said socket having a width greater than the thickness of at least one of the cassettes to be held therein and also having a wall that is upright, and said means for holding X-ray cassettes comprising means in said socket for reducing the width of the socket to a width equal to the thickness of the cassette to be held therein and for applying pressure on the cassette that holds the cassette firmly against said wall of the socket and thereby holds said cassette upright in said socket.

2. A device for holding an X-ray cassette upright and adjacent a body part to be X-rayed, comprising:

means for supporting a body part and an X-ray cassette, said means having an area for receiving a body part to be X-rayed and a cavity that constitutes a socket for receiving an X-ray cassette, said cavity being adjacent to said area, said means including means cooperating with said cavity for holding cassettes of different thicknesses upright in said cavity, said socket having a width greater than the width of at least one of the X-ray cassettes to be held therein and also having an upright wall, and in which said means cooperating with said cavity for holding cassettes of different thicknesses upright comprises means in said cavity for reducing the width of the cavity to the thickness of the X-ray cassette to be held therein and for pressing said cassette against said wall to hold the X-ray cassette upright.

3. A device for firmly holding an X-ray cassette adjacent a body part to be X-rayed, comprising:

support means for supporting a body part to be X-rayed and also having a socket adjacent to a position where the body part may be supported by said means for holding X-ray cassettes of different thicknesses, said socket having a width greater than the thickness of at least one of the X-ray cassettes to be placed in said socket, and pressure applying means in said socket for reducing said width thereby applying a pressure to a portion of an X-ray cassette in said socket to pinch said portion and firmly hold it in a position for receiving X-rays that may be passed through a body part that is supported by said support means.

4. A device as defined in claim 3, in which said pressure applying means includes spring means for applying said pressure to a portion of an X-ray cassette.

5. A device as defined in claim 4, in which said spring means comprises a cam that when rotated applies said pressure to an X-ray cassette and a spring for rotating said cam to apply said pressure.

6. A device as defined in claim 3, in which said pressure applying means comprises clamp means for clamping a portion of an X-ray cassette that is in said socket.

7. A device as defined in claim 6, in which said clamp means comprises threaded means for causing said clamp means to apply a clamping force to an X-ray cassette in said socket.

* * * * *